(12) United States Patent
Molz, IV et al.

(10) Patent No.: US 7,341,587 B2
(45) Date of Patent: Mar. 11, 2008

(54) METHODS AND DEVICES FOR INSERTING AND ENGAGING VERTEBRAL IMPLANTS IN MINIMALLY INVASIVE PROCEDURES

(75) Inventors: Fred J. Molz, IV, Collierville, TN (US); Roy Lim, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 708 days.

(21) Appl. No.: 10/718,072

(22) Filed: Nov. 20, 2003

(65) Prior Publication Data

US 2005/0113832 A1  May 26, 2005

(51) Int. Cl.
*A61B 17/56* (2006.01)

(52) U.S. Cl. .......................... 606/61; 606/99

(58) Field of Classification Search ................ 606/61, 606/99, 104, 107; 623/17.11–17.16
See application file for complete search history.

(56) References Cited

U.S. PATENT DOCUMENTS

| | | | |
|---|---|---|---|
| 4,438,769 A | 3/1984 | Pratt et al. | |
| 4,997,432 A | 3/1991 | Keller | |
| 5,015,247 A | 5/1991 | Michelson | |
| 5,346,115 A | 9/1994 | Perouse et al. | |
| 5,352,219 A | 10/1994 | Reddy | |
| 5,354,292 A * | 10/1994 | Braeuer et al. | 606/1 |
| 5,395,391 A | 3/1995 | Essig et al. | |
| 5,441,059 A | 8/1995 | Dannan | |
| 5,452,733 A | 9/1995 | Sterman et al. | |
| 5,454,814 A | 10/1995 | Comte | |
| 5,458,608 A | 10/1995 | Wortrich | |
| 5,464,447 A | 11/1995 | Fogarty et al. | |
| 5,613,937 A | 3/1997 | Garrison et al. | |
| 5,618,287 A | 4/1997 | Fogarty et al. | |
| 5,688,276 A | 11/1997 | Shaffer | |
| 5,690,648 A | 11/1997 | Fogarty et al. | |
| 5,735,842 A | 4/1998 | Krueger et al. | |
| 5,772,661 A | 6/1998 | Michelson | |
| 5,788,713 A | 8/1998 | Kubach et al. | |
| 5,947,970 A | 9/1999 | Schmelzeisen et al. | |
| 5,957,927 A | 9/1999 | Magee et al. | |
| 6,036,692 A | 3/2000 | Burel et al. | |
| 6,113,605 A | 9/2000 | Storer | |
| 6,156,037 A | 12/2000 | LeHuec et al. | |
| 6,159,200 A | 12/2000 | Verdura et al. | |
| 6,165,184 A | 12/2000 | Verdura et al. | |
| 6,325,805 B1 | 12/2001 | Ogilvie et al. | |

(Continued)

FOREIGN PATENT DOCUMENTS

WO  WO 02/17823 A1  3/2002

(Continued)

*Primary Examiner*—Eduardo C. Robert
*Assistant Examiner*—Michael J Araj
(74) *Attorney, Agent, or Firm*—Krieg DeVault LLP

(57) ABSTRACT

A surgical instrument assembly includes an inserter instrument and a driving instrument to engage an implant to a bony structure in a patient. The inserter instrument is positionable in a patient with the implant engaged thereto to position the implant at an operative site in the patient. A driving instrument is engageable to the inserter instrument to engage the implant to bony structure at the operative site. A template is provided and engageable by the driving instrument to facilitate preparation of the bony structure to receive the implant.

37 Claims, 7 Drawing Sheets

U.S. PATENT DOCUMENTS

| | | |
|---|---|---|
| 6,406,480 B1 | 6/2002 | Beyar et al. |
| 6,428,541 B1 | 8/2002 | Boyd et al. |
| 6,447,512 B1 | 9/2002 | Landry et al. |
| 6,451,054 B1 | 9/2002 | Stevens |
| 6,530,926 B1 | 3/2003 | Davison |
| 6,830,570 B1 * | 12/2004 | Frey et al. .................... 606/61 |
| 2001/0021853 A1 | 9/2001 | Heckele et al. |
| 2002/0045904 A1 | 4/2002 | Fuss et al. |
| 2002/0091390 A1 | 7/2002 | Michelson |
| 2002/0116009 A1 * | 8/2002 | Fraser et al. .................. 606/99 |
| 2003/0208203 A1 | 11/2003 | Lim et al. |

FOREIGN PATENT DOCUMENTS

WO    WO 03/026513 A1    4/2003

* cited by examiner

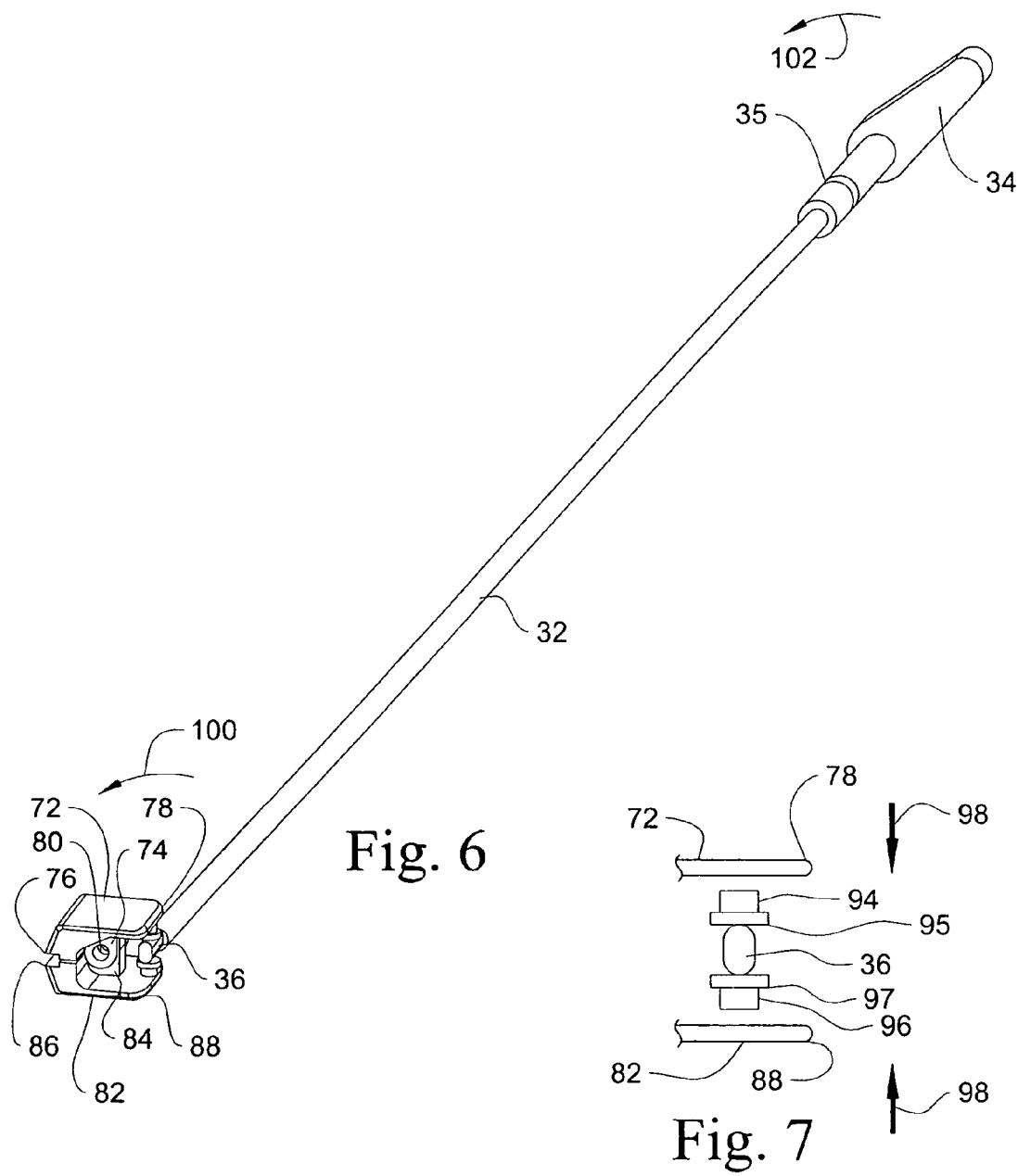

METHODS AND DEVICES FOR INSERTING AND ENGAGING VERTEBRAL IMPLANTS IN MINIMALLY INVASIVE PROCEDURES

BACKGROUND

Various instruments and methods have been developed for surgical procedures for inserting and engaging vertebral implants in a patient. Such procedures include making incisions and retracting skin and tissue to expose the surgical site to access the implantation location. Such procedures can further include providing an access portal at a vertebral level to be accessed for engagement with an implant.

One problem associated with such procedures is the invasiveness of the surgery required to accommodate insertion of implants to locations deep within the patient's body. In open procedures, the exposure is greatest since the skin, tissue and even bone are excised and retracted to expose the implantation location. The invasiveness further complicates the procedure when multiple vertebral levels are to be accessed through multiple access portals.

There remains a need for instruments and methods that can be employed to reduce the invasiveness and complication of surgical procedures for engaging one or more implants to one or more vertebrae along the spinal column.

SUMMARY

A surgical instrument assembly and method for positioning implants along one or more vertebral levels is provided that minimizes the invasiveness of the procedure. An inserter instrument can be releasably engaged to an implant to position the implant into the patient through a first portal. The inserter instrument is operable to orient the implantation axis of the implant in a desired orientation. A driving instrument can be positioned into the patient through a second portal to drive the implant into the bony structure.

A number of implants can be engaged to vertebrae at a number of levels along the spinal column by inserting the implants through the same access portal with the inserter instrument. The inserter instrument can be angled through the access portal to position the implant at any one of a number of vertebral levels, and is operable to orient and implantation axis of the implant at the desired orientation relative to the selected vertebral level. The driving instrument is inserted through a second portal aligned with the vertebral level and the implantation axis of the implant to drive the implant into one or more vertebrae at the vertebral level. This procedure can be repeated with a portal formed for the driving instrument at each vertebral level to be instrumented while only a single portal is employed for insertion of the multiple implants. The driving instrument portals can be small in size, such as is provided with a stab wound, to further minimize the invasiveness of the procedure.

In one specific application, the inserter instrument, driving instrument and implant are employed in a mini-thoracotomy procedure to laterally stabilize multiple thoracic vertebral levels with implants. In one form, the implants are staples. However, applications in other regions of the spine and in other approaches to the spine are also contemplated.

Other aspects, forms, embodiments, objects, features, applications and advantages will also be apparent from the following description.

BRIEF DESCRIPTION OF THE FIGURES

FIG. 6 is a perspective view of a distal portion of the inserter instrument.

FIG. 7 is an end view of the distal portion of FIG. 6.

DESCRIPTION OF THE ILLUSTRATED EMBODIMENTS

Figure 1:
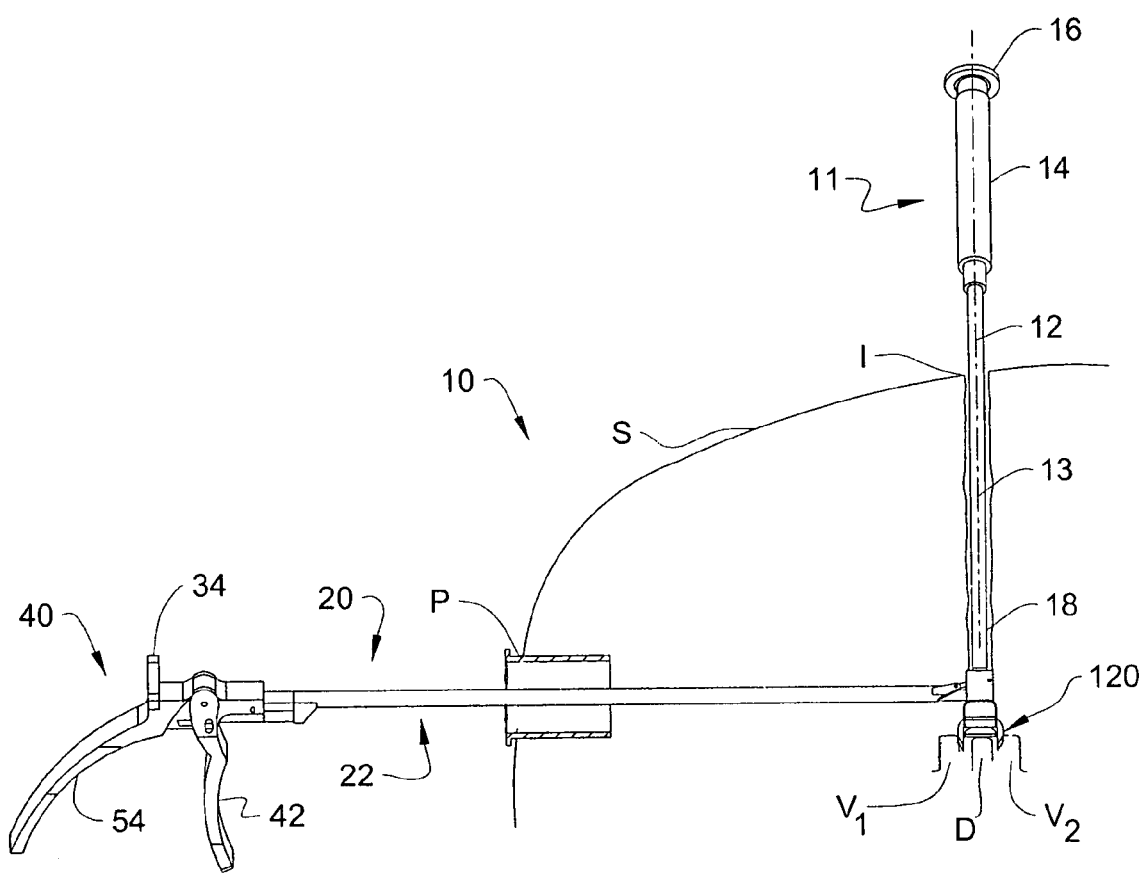
FIG. 1 is a perspective view of a surgical instrument assembly positioned in a patient in a surgical procedure.

For the purposes of promoting an understanding of the principles of the invention, reference will now be made to the embodiment illustrated in the drawings and specific language will be used to describe the same. It will nevertheless be understood that no limitation of the scope of the invention is thereby intended. Any such alterations and further modifications in the illustrated device and any such further applications of the principles of the invention as illustrated therein are contemplated as would normally occur to one skilled in the art to which the invention relates.

Referring now to FIG. 1, there is illustrated a surgical instrument assembly 10 for use in spinal surgeries on a patient. Surgical instrument assembly 10 has application in minimally invasive approaches in insufflated or non-insufflated working spaces, in open surgical procedures, in microsurgeries, and through access sleeves, for example. In one specific application, surgical instrument assembly 10 is used in surgical procedures that require accessing the spine from multiple minimally invasive approaches. However, it should be understood that surgical instrument assembly 10 also has application in other types of surgeries and in other locations of the body.

Surgical instrument assembly 10 includes a driving instrument 11 and an inserter instrument 20. Inserter instrument 20 is releasably engageable to an implant 120 to position implant 120 in a desired location in the patient's body. Driving instrument 11 can be manipulated to deliver a driving force to implant 120 and engage it to a bony structure of a patient. Inserter instrument 20 is operable to remotely manipulate the position of an implantation axis of implant 120 in alignment with a driving axis of driving instrument 11. After engagement of implant 120 in the patient, driving instrument 11 can be removed, and inserter instrument 20 can be disengaged from implant 120 for withdrawal from the patient. In the illustrated embodiment, implant 120 is a staple that includes at least one first prong engageable to a first vertebra V1 and at least one second prong engageable to a second vertebra V2. Further examples of staples are provided in U.S. Pat. No. 6,325,805, which is incorporated herein by reference in its entirety.

Vertebrae V1 and V2 are positioned on opposite sides of disc space D. Vertebrae V1 and V2 and disc space D, as well as other vertebral levels of the spinal column, are accessible through access port P extending through the skin S and underlying tissue of the patient. Access port P can be formed by a sleeve, as shown, or other suitable instrument, such as a rigid sleeve, flexible sleeve, retractor or micro-incision, for example. In any event, port P forms an opening of sufficient cross-sectional area to permit passage of implant 120 therethrough. Inserter instrument 20 can be angled through access port P to position its distal end adjacent a selected one of the vertebral levels to be instrumented. Further examples of instruments, access ports and minimally invasive procedures are discussed in U.S. patent application Ser. No. 09/963,143, filed Sep. 25, 2001, and U.S. patent application Ser. No. 10/202,918 filed Jul. 25, 2002, each of which is incorporated herein by reference in its entirety.

Driving instrument 11 includes a shaft 12 extending along a driving axis 13. Shaft 12 includes a proximal handle portion 14 and an impaction head 16 at the proximal end of handle portion 14. Shaft 12 extends from handle portion 14 to a distal end 18. Distal end 18 is engageable to one or both of inserter instrument 20 and implant 120 to deliver a driving force to implant 120 and engage it to vertebrae V1 and V2. Driving instrument 11 is insertable through a minimally invasive access port I, and is extendable therethrough along a driving axis 13 that is aligned with an implantation axis of implant 120. Access port I can be formed by a stab or puncture wound through skin S and the underlying tissue to minimize trauma thereto. With inserter instrument 20 maintaining implant 120 in the desired location and orientation relative to vertebrae V1 and V2, driving instrument 11 can be inserted through access port I to deliver an impaction force that engages implant 120 to vertebrae V1 and V2.

Inserter instrument 20 is manipulatable through access port P to position implant 20 at any vertebral level within the range of movement and angulation of inserter instrument 20 through access port P. Inserter instrument 30 includes a holding assembly 70 releaseably engageable to implant 120. Holder assembly 70, and thus implant 120, are remotely movable with a handle assembly 40 operably coupled to holding assembly 70 with a shaft assembly 22. The holder assembly 70 can be remotely moved to align the implantation axis of implant 120 as desired for engagement of the implant with at least one vertebra at the selected vertebral level. Accordingly, multiple vertebral level implant engagement procedures can be conducted with each implant being inserted through access port P and positioned at the desired vertebral level. An additional access port I can be formed at each vertebral level to accommodate insertion of driving instrument 11 in alignment with the implantation axis of a particular implant 120.

Inserter instrument 20 includes shaft assembly 22 extending between distal implant holder assembly 70 and proximal handle assembly 40. Handle assembly 40 is operable by the surgeon to remotely manipulate holder assembly 70 through shaft assembly 22 and position implant 120 at the desired orientation in the patient. Holder assembly 70 is removably engageable to implant 120, and provides a platform for engagement by driving instrument 11 to drive implant 120 into an anatomical structure positioned deep within the patient's body, such as vertebrae V1 and V2. With implant 120 engaged to the patient, implant 120 can be remotely released and inserter instrument 20 and driving instrument 11 removed from the patient.

Figure 2:
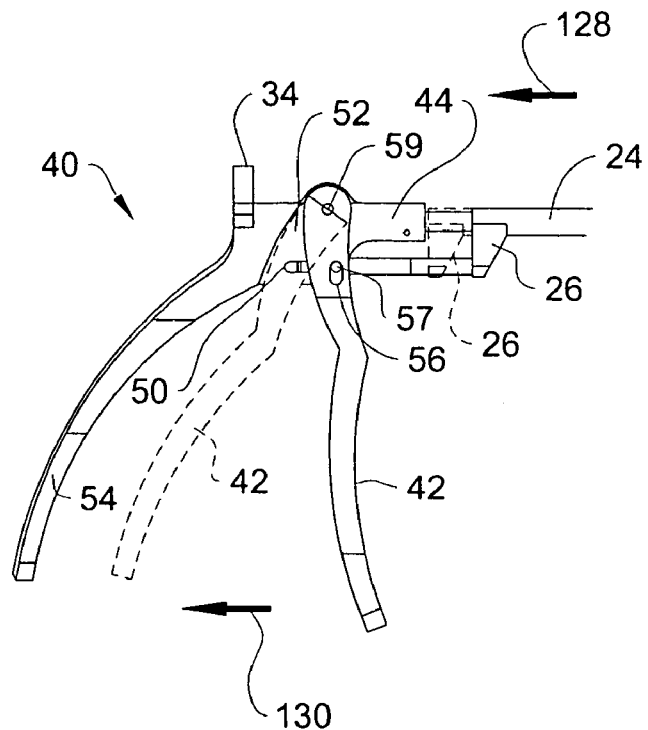
FIG. 2 is a side elevational view of a proximal portion of an inserter instrument comprising a portion of the surgical instrument assembly of FIG. 1.
Figure 3:
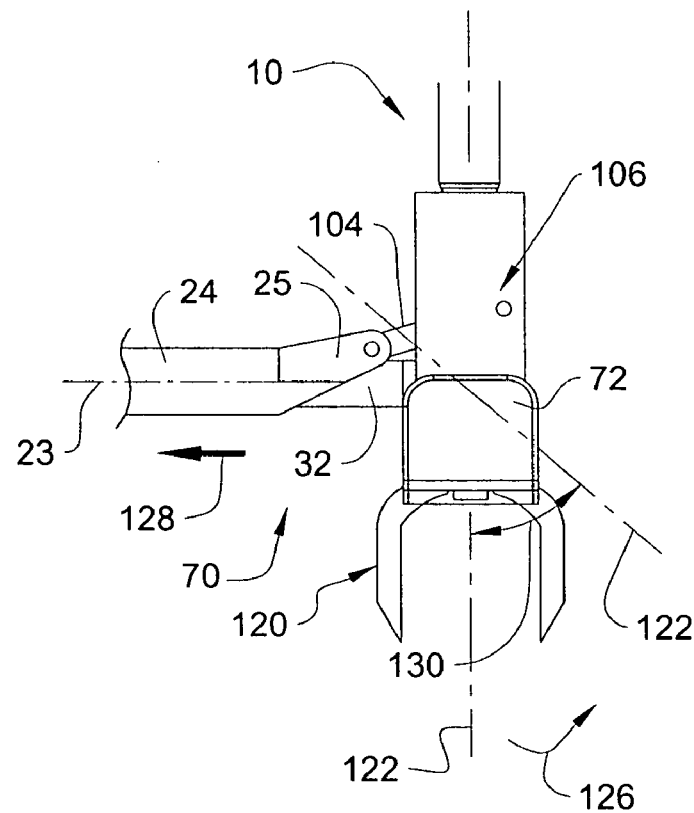
FIG. 3 is a side elevational view of a distal portion of the inserter instrument of FIG. 2.

In FIG. 2, there is shown proximal handle assembly 40 that includes a first handle 42 pivotally mounted to a second handle 54. Shaft assembly 22 includes a first member 24 and a second member 32 extending along a longitudinal axis 23. In the illustrated embodiment, first member 24 is an elongated, hollow tube movably positioned about second member 32, and coupled with first handle 42. Second member 32 is an elongated rod rotatably coupled to second handle 54. First member 24 is movable with first handle 42 along longitudinal axis 23 by pivoting first handle 42 proximally in the direction of arrow 130 relative to second handle 54, as shown in FIG. 2 and as indicated in dashed lines. This proximal movement of first handle 42 pulls first member 24 proximally relative to second member 32, as indicated by arrows 128 in FIGS. 2 and 3.

Figure 4:
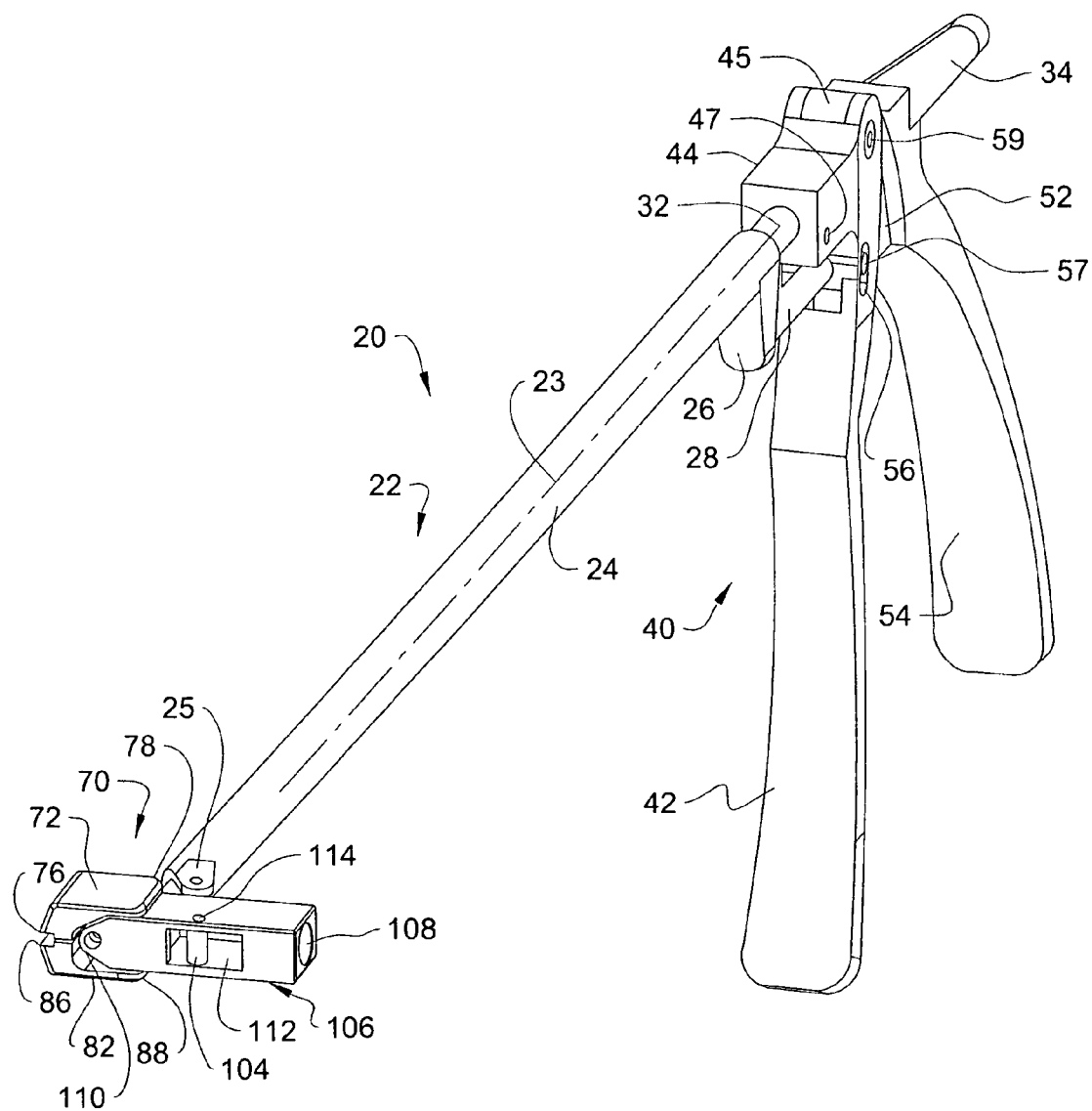
FIG. 4 is a perspective view of the inserter instrument.

The distal end of first member 24 is pivotally linked to a housing member 106 of holder assembly 70 with a linking member 104. Implant 120 is engaged to holder assembly 70 with clamping members 72, 82 (FIG. 4). Implant 120 defines an implantation axis 122 along which implant 120 is moved with driving instrument 11 to engage it to the bony structure of the patient. As indicated by arrow 126 in FIG. 3, proximal movement of first handle 42 and thus first member 24 causes link member 104 to pull on housing member 106 and pivot holder assembly 70 about the distal end of second member 32. This pivoting movement of holder assembly 70 repositions implant 120 and its implantation axis 122 at any orientation relative to longitudinal axis 23 along a path defined by angle 130. It is contemplated that angle 130 can range from 0 up to about 90 degrees. It is further contemplated that the orientation of implantation axis 122 can range from an orthogonal orientation relative to longitudinal axis 23 to an orientation nearly co-linear with longitudinal axis 23.

Referring now generally to FIGS. 4-8, further details of inserter instrument 20 will be discussed. As shown in FIG. 6, second member 32 includes a proximal end with an actuating lever 34 and a proximal coupling portion 35 extending along second member 32. Second member 32 extends to a distal end that includes a camming member 36. Camming member 36 includes a cross-sectional profile that provides movement of engagement members 94, 96 between extended positions, as shown in FIG. 6, and retracted positions, as shown in FIG. 7.

Figure 5:
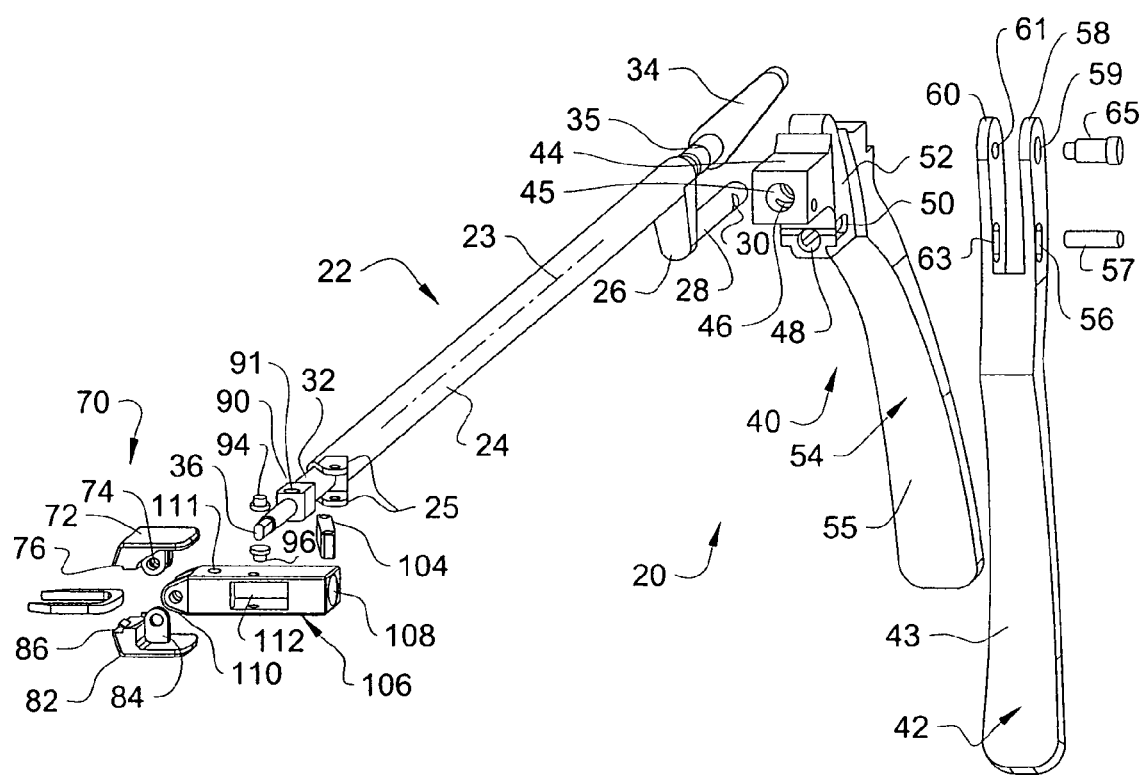
FIG. 5 is an exploded perspective view of the inserter instrument.
Figure 8:
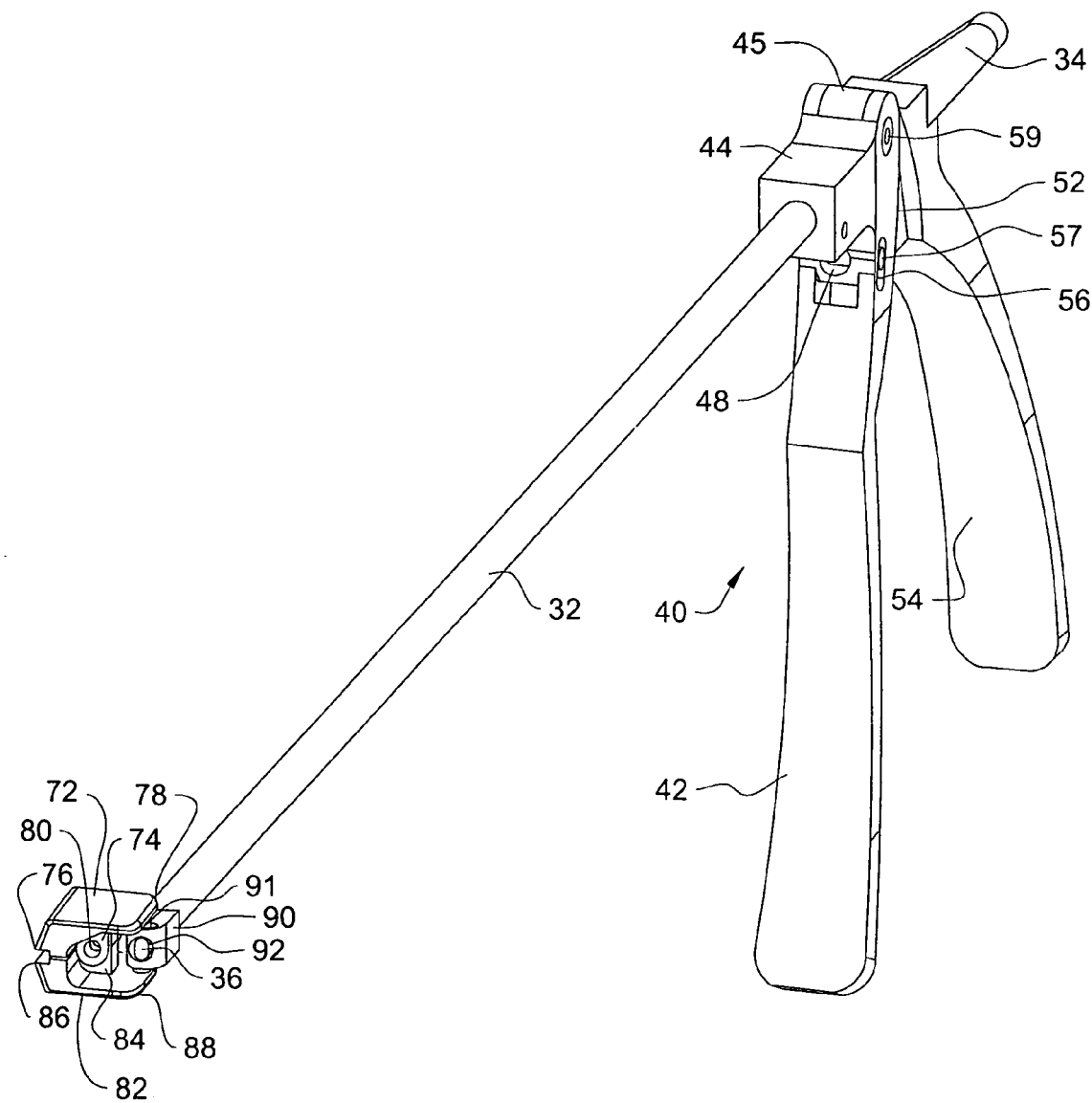
FIG. 8 is a perspective view of a perspective view of the inserter instrument with the driver tool engaging portion removed.

As also shown in FIGS. 5 and 8, first clamping member 72 includes a central ear 74, a distal gripping portion 76, and a proximal extension 78. Similarly, second clamping member 82 includes a central ear 84, a distal gripping portion 86, and a proximal extension 88. Central ears 74, 84 overlap to define a pin receptacle 80 to receive a coupling pin to pivotally couple clamping members 72, 82 to one another. Gripping portions 76, 86 are movable toward one another by pivoting about pin receptacle 80 to grip or hold an implant 120 therebetween. Gripping portions 76, 86 are movable away from one another by pivoting about pin receptacle 80 to release an implant 120 engaged therebetween.

When assembled, engagement member 94, 96 each include an enlarged end 95, 97, respectively, that engages camming member 36 along an adjacent side thereof. Camming member 36 is movable to an actuating position, as shown in FIG. 6, where camming member 36 is oriented with its elongated cross-sectional dimension positioned to move engagement members 94, 96 away from one another. In the actuated position engagement members contact the adjacent one of the proximal extensions 78, 88 of clamping members 72, 82. Clamping members 72, 82 are pivoted about the pin in receptacle 80 to position gripping portions 76, 86 adjacent one another and into contact with an implant positioned therebetween. Gripping portions 76, 86 define a receptacle therebetween that conforms to the outer surface profile of implant 120. In the illustrated embodiment, implant 120 and thus the receptacle define a rectangular cross-section, although other shapes are contemplated.

To release the implant, actuator 34 is manipulated as indicated by arrow 102 to rotate second member 32 and thus camming member 36 90 degrees so that enlarged ends 95, 97 of engagement members 94, 96 are in contact with the shortened cross-sectional dimension of camming member 96. This allows clamping members 72, 82 to pivot in the opposite direction about the pin in receptacle 80, as indicated by arrows 98, thus moving gripping portions 76, 86 away from one another to release an implant engaged therebetween.

As shown in FIGS. 4 and 5, holder assembly 70 further includes housing member 106 in the form of an elongate tubular member with a proximal end opening 108. A cavity 112 extends from proximal end opening 108 and opens between distal fingers 110. Clamping members 72, 82 are pivotally mounted between distal fingers 110 with the pivot pin extending through receptacle 80 and engaged to distal fingers 110. Link member 104 extends through a side opening of housing member 106, and is pivotally coupled thereto in cavity 112. Link member 104 is further pivotally coupled at its opposite end to ears 25 extending from one side of first member 24.

As shown in FIGS. 5 and 8, an engagement member retainer 90 is slidably positioned about second member 32. Engagement members 94, 96 are movably captured in retainer 90, and project through corresponding ones of the openings 91 therethrough. Retainer 90 is positionable in cavity 112 of housing member 106 with engagement members 94, 96 aligned with and extending into openings 111 of housing member 106. It is contemplated that engagement members 94, 96 extend through openings 111 and pivotally couple housing member 106 to the distal end of second member 32. Accordingly, as link member 104 is moved proximally or distally by movement of first member 24 with handle assembly 40, housing member 106 pivots about engagement members 94, 96.

As shown in FIGS. 4, 5 and 8, handle assembly 40 includes first handle 42 with a lower gripping portion 43 and upper extensions 58, 60. Upper extensions 58, 60 each include an upper hole 59, 61, respectively, extending therethrough transversely to longitudinal axis 23. A slot between upper extensions 58, 60 accommodates positioning of first handle 42 about a body portion 44 of second handle 54. Upper extensions 58, 60 each further include a lower vertically elongated hole 56, 63, respectively.

Second handle 54 includes a lower gripping portion 55 and an axially extending body portion 44 extending in the direction of longitudinal axis 23. Second handle 54 includes lateral recessed portions 52 which receive upper extensions 58, 60 of first handle 42 therein. A laterally extending hole (not shown) through body portion 44 communicates between recessed portions 52, and receives a pin 65 to pivotally couple first handle 42 to second handle 54.

Body portion 44 further includes a lower, axially extending passage 48 and a laterally extending slot 50 in communication therewith. Slot 50 extends between recessed portions 52. First member 24 of shaft assembly 22 includes an offset arm 26 extending transversely thereto, and a drive arm 28 extending from offset arm 26 in a direction parallel to longitudinal axis 23. Drive arm 28 is positionable in lower passage 48, and includes a proximal notch 30. Drive pin 57 engages drive member 28 in notch 30. Drive pin 57 is slidable along slot 50 as first handle 42 is moved distally and proximally relative to second handle 42. Drive pin 57 moves drive member 28 distally and proximally along lower passage 48, and thus moves first member 24 distally and proximally along second member 32 in response to movement of first handle 42. Drive pin 57 further moves vertically up and down along elongated holes 56, 63 as the angle of first handle 42 changes relative to body portion 44 as it is pivoted relative thereto.

Body portion 44 further includes an upper passage 46 extending therethrough and along longitudinal axis 23 to rotatably receive first member 32 therein. Proximal coupling portion 35 of first member 32 includes a notch to receive a coupling pin 47 extending through body portion 44. Coupling pin 47 prevents distal and proximal movement of second member 32 along longitudinal axis 23, but permits second member 32 to be rotated about longitudinal axis 23 to selectively deploy and retract engagement members 94, 96 for engaging and releasing an implant with clamping members 72, 82, as discussed above. Lever actuator 34 projects proximally from second handle 54 to facilitate access thereto.

Driving instrument 11 is engageable with housing member 106 to deliver an impaction or driving force to implant 120 engaged by clamping members 72, 82. Distal end 18 can include a reduced sized tip positionable into proximal end opening 108, and a distally facing end wall to deliver a driving force to the proximal end wall of housing member 106. It is further contemplated that distal end 18 can be configured to engage housing member 106 via, for example, a ball-detent mechanism, bayonet lock, frictional fit, threaded engagement, interdigitating members in order to facilitate application of proximally directed forces and lateral forces to reposition implant 120 in addition to distally directed driving or impaction forces.

Figure 9:
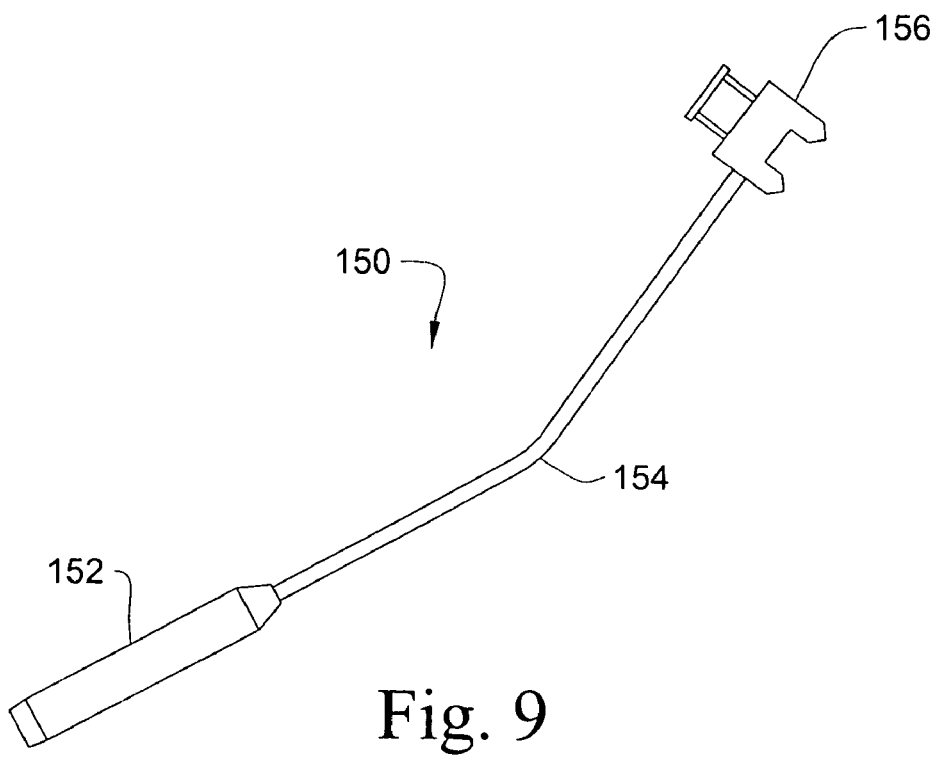
FIG. 9 is an elevation view of an implant template instrument.
Figure 10:
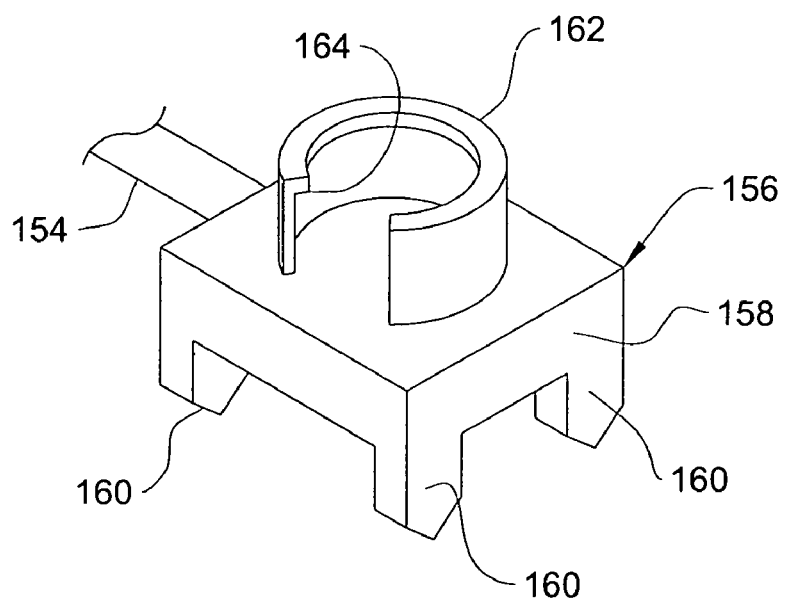
FIG. 10 is a perspective view of a distal portion of the implant template instrument of FIG. 9.

Referring now to FIG. 9, there is shown an implant template instrument 150 to facilitate insertion of a staple implant. Template instrument 150 includes a proximal handle 152, a shaft 154 extending distally from handle 152, and a template portion 156 at a distal end of shaft 154. As shown in FIG. 10, template portion 156 includes a template 158 having markers 160 extending therefrom. Markers 160 are provided in spacing and number that correspond to penetration locations of prongs of a staple implant 120.

Template portion 156 further includes a driving instrument connector 162. Connector 162 includes a partially cylindrical body opening along one side thereof, and an internal lip 164 extending therearound. Connector 162 is engageable with a correspondingly shaped distal portion of driving instrument 11.

Shaft 154 is bendable or malleable to adjust the positioning of template portion 156 relative to handle 152 with shaft 154 extending through access port P. Accordingly, shaft 154 can be manipulated by the surgeon to provide the necessary angulation of shaft 154 to position template 158 at the desired vertebral level in the orientation necessary to embed markers 160 into the vertebra at the locations desired for the prongs of the staple implant 120. Driving instrument 11 is positionable through port I and is engageable with lip 164 of connector 162 to bend shaft 154 when template portion 156 is positioned in the patient. When markers 160 are positioned as desired, driving instrument 11 can be employed to impart a driving force and embed markers 160 into the underlying bone material.

After marking of the vertebrae with template instrument 150, driving instrument is released therefrom. Template instrument 150 can then be withdrawn from access port P. Implant 120 is engaged with inserter instrument 20, and then inserted through access port P. The prongs of a staple implant 120 are aligned with the template markings by manipulating inserter instrument 20. Driving instrument 11 in access port I is engaged with inserter instrument 20, and implant 20 is engaged to the vertebrae.

While the invention has been illustrated and described in detail in the drawings and foregoing description, the same is to be considered as illustrative and not restrictive in character, and that all changes and modifications that come within the spirit of the invention are desired to be protected.

What is claimed is:

1. A surgical instrument assembly for securing an implant to a vertebral level, comprising:
an inserter instrument including a proximal handle assembly, a shaft assembly extending along a longitudinal axis of said inserter instrument and operably coupled between said handle assembly and a distal holder assembly, said holder assembly being removably engageable to the implant and remotely movable with said handle assembly to orient the implant along a selected one of any number of implantation axes, wherein said holder assembly includes a housing member mounted to said shaft assembly, said housing assembly extending proximally from the implant along said selected implantation axis; and
a driving instrument engageable with said holder assembly and adapted to deliver a driving force to said housing assembly to move the implant along said selected implantation axis while said holder assembly is engaged with said implant.

2. The surgical instrument assembly of claim 1, wherein said holder assembly is movable relative to orient said implantation axis at an angle relative to said longitudinal axis.

3. The surgical instrument assembly of claim 2, wherein said orientation ranges from a first position orthogonal to said longitudinal axis to a second position substantially co-linear with said longitudinal axis.

4. The surgical instrument assembly of claim 1, wherein said holder assembly is pivotally coupled about a distal end of said shaft assembly.

5. The surgical instrument assembly of claim 4, wherein said holder assembly includes a pair of clamping members pivotally coupled to one another, said clamping members each including a distal gripping portion, said clamping members pivotal to move said distal gripping portions toward one another to engage the implant received therebetween and further being pivotal to move said distal gripping portions away from one another to release the implant engaged therebetween.

6. The surgical instrument assembly of claim 5, wherein said distal end of said shaft assembly comprises a camming member rotatable about said longitudinal axis between an engagement position and a release position.

7. The surgical instrument assembly of claim 6, comprising a retainer positioned about said camming member and a pair of opposite engagement members positioned in said retainer in contact with said camming member, wherein in said engagement position said engagement members project from said retainer into contact with a proximal extension of an adjacent one of said clamping members to move said distal gripping portions toward one another.

8. The surgical instrument assembly of claim 7, wherein in said release position said engagement members move toward one another into said retainer allowing said proximal extension to move toward one another and pivoting said distal gripping portions away from one another.

9. The surgical instrument assembly of claim 8, wherein:
said housing member is pivotally linked to said shaft assembly;
said clamping members are pivotailly coupled to a distal end of said housing member; and
said retainer is positioned in said housing member, said housing member including openings aligned with and receiving respective ones of the engagement members therethrough in said engagement position and said release position.

10. The surgical instrument assembly of claim 9, wherein said housing member includes a proximal end opening and said driving instrument is engageable in said proximal end opening to deliver said driving force thereto.

11. The surgical instrument assembly of claim 7, wherein said holder assembly is pivotally coupled to said engagement members.

12. The surgical instrument assembly of claim 5, wherein said housing member is pivotally linked to said shaft assembly, said clamping members further being pivotally coupled to a distal end of said housing member.

13. The surgical instrument assembly of claim 12, wherein said housing member includes a proximal end opening and said driving instrument is engageable in said proximal end opening to deliver said driving force thereto.

14. The surgical instrument assembly of claim 1, wherein said shaft assembly includes a first member and a second member, said second member extending through said first member.

15. The surgical instrument assembly of claim 14, wherein said handle assembly includes a first handle pivotally coupled to a second handle, said first member being coupled to said second member and longitudinally movable relative to said second member in response to pivoting movement of said first handle relative to said first handle.

16. The surgical instrument assembly of claim 15, wherein said second member is coupled to said second handle and rotatable relative thereto about said longitudinal axis.

17. The surgical instrument assembly of claim 1, wherein said inserter instrument is insertable through a first port in the patient to position the implant at an implantation location and said driving instrument is insertable through a second, smaller port to engage said holder assembly at the implantation location.

18. A surgical instrument assembly for securing an implant to a vertebral level, comprising:
an inserter instrument including a proximal handle assembly, a shaft assembly extending along a longitudinal axis of said inserter instruments and operably coupled between said handle assembly and a distal holder assembly, said holder assembly being removably engageable to the implant and remotely movable with said handle assembly to orient the implant along a selected one of any number of implantation axes, wherein said holder assembly is pivotally coupled about a distal end of said shaft assembly and includes a pair of clamping members pivotally coupled to one another, said clamping members each including a distal gripping portion, said clamping members pivotal to move said distal gripping portions toward one another to engage the implant received therebetween and further being pivotal to move said distal gripping portions away from one another to release the implant engaged therebetween, wherein said distal end of said shaft assembly comprises a camming member rotatable about said longitudinal axis between an engagement position and a release position; and a driving instrument engageable with said holder assembly and adapted to deliver a driving force to the implant along said implantation axis while said holder assembly is engaged with said implant.

19. The surgical instrument assembly of claim 18, wherein said holder assembly is movable relative to orient said implantation axis at an angle relative to said longitudinal axis.

20. The surgical instrument assembly of claim 19, wherein said orientation ranges from a first position orthogonal to said longitudinal axis to a second position substantially colinear with said longitudinal axis.

21. The surgical instrument assembly of claim 18, comprising a retainer positioned about said camming member and a pair of opposite engagement members positioned in said retainer in contact with said camming member, wherein in said engagement position said engagement members project from said retainer into contact with a proximal extension of an adjacent one of said clamping members to move said distal gripping portions toward one another.

22. The surgical instrument assembly of claim 21, wherein in said release position said engagement members move toward one another into said retainer allowing said proximal extension to move toward one another and pivoting said distal gripping portions away from one another.

23. The surgical instrument assembly of claim 22, wherein:
said holder assembly includes a housing member pivotally linked to said shaft assembly;
said clamping members are pivotally coupled to a distal end of said housing member; and
said retainer is positioned in said housing member, said housing member including openings aligned with and receiving respective ones of the engagement members therethrough in said engagement position and said release position.

24. The surgical instrument assembly of claim 23, wherein said housing member includes a proximal end opening and said driving instrument is engageable in said proximal end opening to deliver said driving force thereto.

25. The surgical instrument assembly of claim 21, wherein said holder assembly is pivotally coupled to said engagement members.

26. The surgical instrument assembly of claim 18, wherein said shaft assembly includes a first member and a second member, said second member extending through said first member.

27. The surgical instrument assembly of claim 26, wherein said handle assembly includes a first handle pivotally coupled to a second handle, said first member being coupled to said second member and longitudinally movable relative to said second member in response to pivoting movement of said first handle relative to said first handle.

28. The surgical instrument assembly of claim 27, wherein said second member is coupled to said second handle and rotatable relative thereto about said longitudinal axis.

29. The surgical instrument assembly of claim 18, wherein said inserter instrument is insertable through a first port in the patient to position the implant at an implantation location and said driving instrument is insertable through a second, smaller port to engage said holder assembly at the implantation location.

30. A surgical instrument assembly for securing an implant to a vertebral level, comprising:
an inserter instrument including a proximal handle assembly, a shaft assembly extending along a longitudinal axis of said inserter instrument and operably coupled between said handle assembly and a distal holder assembly, said holder assembly being removably engageable to the implant and remotely movable with said handle assembly to orient the implant along a selected one of any number of implantation axes, wherein said holder assembly:
is pivotally coupled about a distal end of said shaft assembly;
includes a pair of clamping members pivotally coupled to one another, said clamping members each including a distal gripping portion, said clamping members pivotal to move said distal gripping portions toward one another to engage the implant received therebetween and further being pivotal to move said distal gripping portions away from one another to release the implant engaged therebetween;
includes a housing member pivotally linked to said shaft assembly, said clamping members further being pivotally coupled to a distal end of said housing member; and
a driving instrument engageable with said holder assembly and adapted to deliver a driving force to the implant along said implantation axis while said holder assembly is engaged with said implant.

31. The surgical instrument assembly of claim 30, wherein said housing member includes a proximal end opening and said driving instrument is engageable in said proximal end opening to deliver said driving force thereto.

32. The surgical instrument assembly of claim 30, wherein said shaft assembly includes a first member and a second member, said second member extending through said first member.

33. The surgical instrument assembly of claim 32, wherein said handle assembly includes a first handle pivotally coupled to a second handle, said first member being coupled to said second member and longitudinally movable relative to said second member in response to pivoting movement of said first handle relative to said first handle.

34. The surgical instrument assembly of claim 33, wherein said second member is coupled to said second handle and rotatable relative thereto about said longitudinal axis.

35. The surgical instrument assembly of claim 30, wherein said inserter instrument is insertable through a first port in the patient to position the implant at an implantation location and said driving instrument is insertable through a second, smaller port to engage said holder assembly at the implantation location.

36. The surgical instrument assembly of claim 30, wherein said holder assembly is movable relative to orient said implantation axis at an angle relative to said longitudinal axis.

37. The surgical instrument assembly of claim 36, wherein said orientation ranges from a first position orthogonal to said longitudinal axis to a second position substantially colinear with said longitudinal axis.

* * * * *